United States Patent
Eriksson et al.

(10) Patent No.: US 8,372,469 B2
(45) Date of Patent: Feb. 12, 2013

(54) METHOD FOR PRODUCING A PIEZOELECTRIC FILM

(75) Inventors: Tom Eriksson, Uppsala (SE); Kenth Nilsson, Akersberga (SE); Anna-Karin Johansson, Vallentuna (SE); Karin Lungstrom, Hasselby (SE); Koroush Lashgari, Sundyberg (SE); Annika Pohl, Tyreso (SE); Gunnar Westin, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/547,841

(22) Filed: Jul. 12, 2012

(65) Prior Publication Data

US 2012/0276279 A1 Nov. 1, 2012

Related U.S. Application Data

(62) Division of application No. 11/920,380, filed as application No. PCT/SE2005/000823 on May 31, 2005, now Pat. No. 8,246,929.

(51) Int. Cl.
*B32B 17/00* (2006.01)
(52) U.S. Cl. ............... 427/2.24; 427/126.3; 427/226
(58) Field of Classification Search ............ 427/2.24, 427/126.3, 226; 428/697, 471, 699–702
See application file for complete search history.

(56) References Cited

U.S. PATENT DOCUMENTS

| | | | |
|---|---|---|---|
| 5,011,796 A | 4/1991 | Bridger et al. | |
| 5,527,480 A | 6/1996 | Bailey et al. | |
| 5,824,419 A * | 10/1998 | Kawai et al. | 428/432 |
| 6,140,746 A | 10/2000 | Miyashita et al. | |
| 6,526,984 B1 | 3/2003 | Nilsson et al. | |
| 6,571,130 B1 | 5/2003 | Ljungstrom et al. | |
| 2003/0141783 A1 | 7/2003 | Klee et al. | |
| 2003/0178605 A1 | 9/2003 | Nonoyama et al. | |

FOREIGN PATENT DOCUMENTS

WO 00/67300 * 11/2000

OTHER PUBLICATIONS

Derderian, et al., "Microstructure/Process Relations in Sol-Gel Prepared KNbO3 Thin Films on (100) MgO" 1994, J. Am. Ceram. Soc. 77(3), pp. 820-828.*
Egerton, L. et al., "Piezoelectric and Dielectric Properties of Ceramics in the System Potassium—Sodium Niobate," Journal of the American Ceramic Society. 1959;42(9):438-442.
Jaeger, R.E et al., "Hot Pressing of Potassium-Sodium Niobates," America Ceramic Society Bulletin. May 1962;45:209-213.
Egerton, L. et al., "Isostatically Hot-Pressed Sodium-Potassium Niobate Transducer Material for Ultrasonic Devices," Ceramic Society Bulletin. 1968;47:1151-1156.
Cho, Choong-Rae et al., "Self-assembling ferroelectric Na0.5K0.5NbO3 thin films by pulsed-laser deposition," Applied Physics Letters. Jul. 1999;75(2):268-270.
Margolin, A.M. et al., "(K,Na)NbO3 ferroelectric films synthesized by cathode sputtering," Soy. Phys. Tech. Phys. Dec. 1988;33(12)1435-1438.
Ichiki, M. et al., "Electrical properties of piezoelectric sodium-potassium niobate," Journal of the European Ceramic Society. 2004;24(6):1693-1697.
Cho, Choong-Rae, "c-Axis oriented Na0.5K0.5NbO3 thin films on Si substrates using metalorganic chemical vapor deposition," Materials Letters. Dec. 2002;57:781-786.
Brinker, C. Jeffrey et al., "Sol-Gel Science," Table of Contents. Dec. 1990.
Restriction Requirement, mailed Oct. 3, 2011—Parent U.S. Appl. No. 11/920,380.
NonFinal Office Action, mailed Dec. 5, 2011—Parent U.S. Appl. No. 11/920,380.
Final Office Action, mailed Apr. 4, 2012—Parent U.S. Appl. No. 11/920,380.
Notice of Allowance, mailed May 11, 2012—Parent U.S. Appl. No. 11/920,380.

* cited by examiner

*Primary Examiner* — Steven Bos (57) ABSTRACT

A method for producing a biocompatible material of the formula $Na_xK_yNbO_3$, $0 \leq x \leq 0.8$, $0.2 \leq y \leq 1$, $x+y=1$ includes the steps of a) providing a Na-precursor and a K-precursor for $Na_xK_yNbO_3$, b) mixing the precursors in solution wherein said precursors first react to form a sol and thereafter a gel, c) heat treating the gel to obtain an oxide of the material $Na_xK_yNbO_3$, $0 \leq x \leq 0.8$, $0.2 \leq y \leq 1$, $x+y=1$. The material can be produced as a film, and the material or film can be provided on the exterior surface of a medical implant that will come into contact with body tissue and/or body fluids upon implantation thereof.

19 Claims, 9 Drawing Sheets

Figure 9

METHOD FOR PRODUCING A PIEZOELECTRIC FILM

CROSS REFERENCE TO RELATED APPLICATIONS

This is a division of U.S. patent application Ser. No. 11/920,380, filed Jan. 26, 2009, which claims priority from International Application No. PCT/SE2005/000823, filed May 31, 2005.

FIELD OF THE INVENTION

The invention refers to a new method for preparing a biocompatible material with the formula $Na_xK_yNbO_3$ (sodium potassium niobate), as well as a material and a film prepared by the method, and a piezoelectric implant comprising the biocompatible material.

BACKGROUND OF THE INVENTION

Piezoelectric materials have a widespread use in the medical field. The materials have for instance found use in electrodes and sensors for implantation in the human or animal body.

The piezoelectric materials used in the medical field for sensing purposes or for mechanical stimulation must meet high standards in regard of for instance sensitivity and durability. One consequence of this is that many prior art piezoelectric materials are less suitable for this purpose.

A piezoelectric material that is often used is lead zirconium titanate (PZT). However, this material has some recognized drawbacks and handling problems. Commonly occurring problems with PZT are inhomogeneous phases, reactions with the substrate, impurities of pyrochlore type and PbO formation at the surface. This is mainly due to the chemistry of lead: it has a low melting point and is easily reduced. This can lead to formation of Pb droplets in the material during the synthesis and shortage of Pb in the active material, which reduces the piezoelectricity. It can be noted, that an excess of Pb is often used in the synthesis to obtain the right composition in the PZT material. Further, PZT deposition on a Pt substrate (commonly used for implantation) is not recommended, since Pb alloys with Pt.

NKN (Sodium potassium niobate) does not exhibit these drawbacks. It does not alloy with Pt, and NKN can be heat treated at a higher temperature than PZT (NKN: 1000° C.; PZT: 500° C.).

WO99/54266 discloses a biocompatible ceramic material for implants comprising $Na_xK_yNbO_3$, $0 \leq x \leq 0.8$, $0.2 \leq y \leq 1$, x+y=1. The object of this invention is to provide a long-term stable material that can be wholly or selectively polarized in order to obtain piezoelectric properties for tissue growth promoting purposes. WO99/53972 discloses a piezoelectric implant comprising $Na_xK_yNbO_3$, $0 \leq x \leq 0.8$, $0.2 \leq y \leq 1$, x+y=1. The object of this disclosure is to provide an implant that has a sensitivity and a durability that meet the high standards required and which further is biocompatible.

Thus, NKN is known and has also shown excellent properties for use in implants. In addition, it is possible to polarize the material in order to provide it with piezoelectric properties. The material combines a very high level of biocompatibility, mechanical and chemical stability that are expected to be at least ten years, a piezoelectricity constant d33 that can exceed 100 pC/N, resistivity that can exceed $10^{12}$ Ωm, and a Curie temperature >160° C. The material will function as desired at a working temperature of 36-41° C., and a band width of 0.3-20 Hz. Thus, NKN is a highly desired piezoelectric material within this field The conventional NKN-preparation methods include:
(1) calcinations and milling together with sintering, where however milling often brings contaminations from the milling equipment. Also, sintering may lead to oxygene defects in the material, which seem to be a result of the choice of sample holder during the sintering process. Moreover, sintering can e.g. be air-fired, hot pressed or made by hot isostatic pressure. The NKN-material can e.g. be made as a bulk material by means of the hot isostatic pressing methods using sodium carbonate, potassium carbonate and niobium pentoxide as precursors as defined in the following articles from American Ceramic Society Bulletin: Egerton-Dillon in 42 (1959) pp 438-442, Jaeger-Egerton in 45 (1962) pp 209-213 and Egerton-Bieling in 47 (1968) pp 1151-1156. Normally hot pressed materials give a higher $d_{33}$-value (measure of piezoelectricity) than air-fired;
(2) pulsed laser deposition (PLD) or laser ablation, having the drawback that Na- and K-compounds are volatile, which may lead to Na- and/or K-deficiency in the material (Self-assembling ferroelectric Na0.5K0.5NbO3 thin films by pulsed laser deposition" Choong-Rae Cho, Alex Grishin, Appl. Phys. Lett. 75, 268 (1999));
(3) sputtering (e.g. Rf-magnetron sputtering), whereby the major drawback of Rf-magnetron is oxygen defects in the material, sometimes together with a $Na_2Nb_4O_{11}$-contamination. The NKN-material may also be made in the form of films or layers on substrates by means of cathode sputtering methods as for instance described in Margolin et al, "(K, Na)NbO$_3$ ferroelectric films synthesized by cathode sputtering", Sov. Phys. Tech. Phys. 33(12), December 1988, or by other suitable thin film techniques;
(4) solid-state reaction methods (sometimes with a subsequent hot pressing) (see e.g. Ichiki et al., Journal of the European Ceramic Society, 2004, 24; 6:1693-97). By using this method, the synthesis requires a relatively long time. Also, it is difficult to obtain a homogenous composition; or
(5) chemical vapor deposition (CVD) (Choong-Rae, Materials Letters, 2002, 57; 4:781-786). In this disclosure, a NKN-film is deposited from precursors that are pre-evaporated at 700-750° C. However, the NKN material that is disclosed exhibit Nb deficiencies (the composition is estimated to comprise Na:K:Nb 1.00:1.00:1.47). Further, a mixture of NKN and the Si-substrate occurs in the interface, which results in a varying NKN composition.

With conventional NKN-production methods it is common with oxygen defects and other material problems. NKN having oxygene defects are often treated in oxygene in order to fill the defects, but that results in an additional production step, which makes the production more expensive. Also, for bulk material it is often difficult to remove the defects in the entire material.

Moreover, a common problem when using conventional synthesis methods for piezoelectric materials and NKN, is that the methods make it difficult to control the composition. This results in low phase purity, in a low piezoelectric effect, if any. Further, this makes it difficult to produce a thin piezoelectric film (which often is desirable in e.g. sensor applications) having reliable physical and chemical properties, since the material characteristics are varying and/or unpredictable.

SUMMARY OF THE INVENTION

Accordingly, there is a strong need in the art for a novel way of providing NKN that makes it easier to control the composition that is synthesized, and further solving other problems with prior art methods and compositions.

An object of the present invention is to provide a method that solves the problems of the prior art, and which method makes it possible to provide a biocompatible NKN-material having the desired characteristics.

The above object is achieved in accordance with the invention by a method for producing a biocompatible material with the formula $Na_xK_yNbO_3$, $0 \leq x \leq 0.8$, $0.2 \leq y \leq 1$, $x+y=1$ by using a sol-gel synthesis.

In accordance with the invention a so-called "sol-gel"-method is used for producing the NKN-material (Brinker and Scherer, Sol-Gel Science, Academic Press, 1990). The sol-gel method makes it easier to control the synthesized composition. General advantages with the sol-gel method include
(i) simple technique,
(ii) low processing temperatures can be used,
(iii) the stoichiometry is easily controlled,
(iv) gives highly homogenous products and
(v) large areas can be uniformly coated.

Furthermore, NKN prepared by sol-gel also has proved to have a strong adhesion to the substrate.

Thus, the present invention provides a method that is efficient and that results in a NKN-material having a good homogeneity. Moreover, it is easier to obtain a uniform NKN film than by using prior art methods.

The above object also is achieved in accordance with the invention by a method for producing a film by using a sol-gel synthesis embodying the biocompatible material of the invention described above.

In accordance with the invention a film having a desired thickness is readily provided. By using the present invention it is possible to form a film having a thickness with a preferred thickness of 0.1-10 μm.

The above object also is achieved in accordance with the invention by a biocompatible material comprising $Na_xK_yNbO_3$, $0 \leq x \leq 0.8$, $0.2 \leq y \leq 1$, $x+y=1$, obtained by the method according to the invention described above.

The above object also is achieved in accordance with the invention by a biocompatible film essentially composed of the biocompatible material of the invention described above.

The above object also is achieved in accordance with the invention by an implant that may come into contact with body tissue and/or body fluids, comprising the biocompatible material of the invention or the biocompatible film of the invention.

DESCRIPTION OF THE PREFERRED EMBODIMENTS

The present invention involves the use of a sol-gel synthesis for preparing a biocompatible material.

Sol-gel is a soft chemistry synthesis method that is commonly used for producing ceramics, nano-sized particles, or thin material layers. Mixing metal-alkoxides (M-OR) with water, at the right pH, forms a gel by hydrolysis. A coating technique is normally used to apply the gel onto a substrate, e.g. dip-coating, spray-coating or spin-coating.

Figure 1:
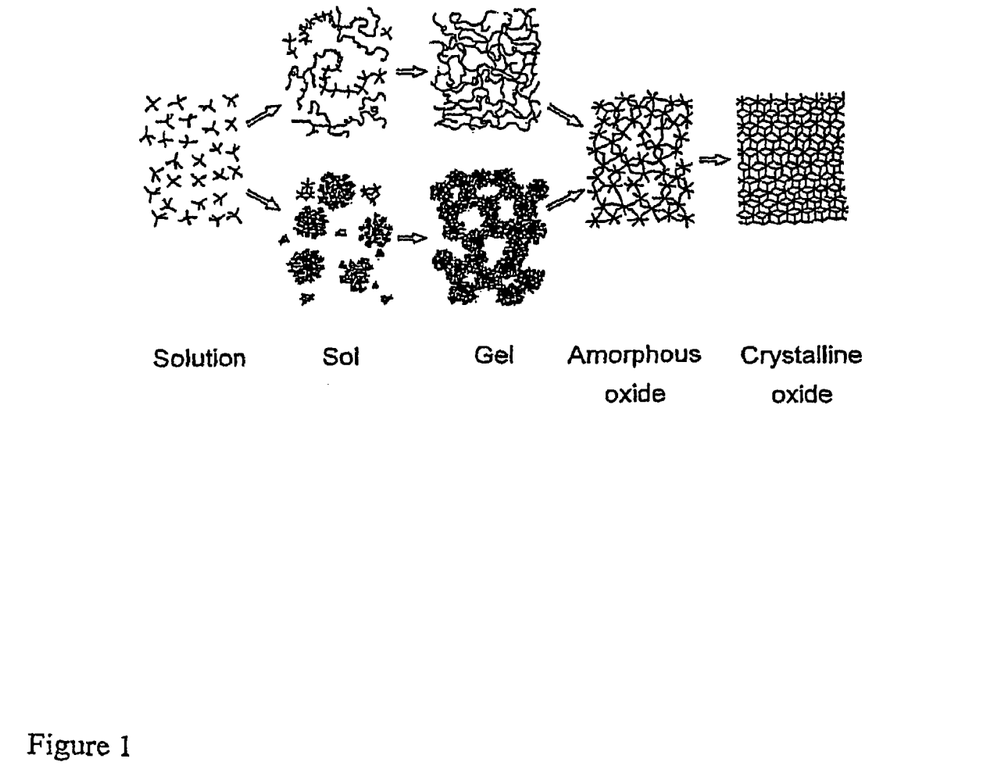
FIG. 1 is a picture of the sol-gel synthesis wherein the molecules are mixed in a solution and reactions are initiated and first a sol is formed, i.e. a suspension of small particles in the solution, and then the gel is annealed to form an oxide.

Preparation of materials with complicated compositions from solutions has many advantages, e.g. high purity, moderate preparation temperatures and excellent possibilities to control the composition. Metal-organic sol-gel synthesis is used as an example in this invention. This is based on reactive metal-organic compounds that are dissolved and mixed in organic solvents, which form a solid oxide-based network, i.e. a gel, by addition of water. The gel is then annealed to obtain the preferred oxide. The composition mixture of the compounds in the solution can be maintained in the oxide if the temperature treatment is made in a controlled way. (FIG. 1).

In a first aspect the invention provides a method for producing a biocompatible material with the formula $Na_xK_yNbO_3$, $0 \leq x \leq 0.8$, $0.2 \leq y \leq 1$, $x+y=1$, comprising the steps of:
(a) providing a Na-precursor and a K-precursor for $Na_xK_yNbO_3$;
(b) mixing the precursors in solution, whereby they first react to form a sol and thereafter a gel;
(c) heat treating the gel to obtain an oxide of the material $Na_xK_yNbO_3$, $0 \leq x \leq 0.8$, $0.2 \leq y \leq 1$, $x+y=1$.

The NKN material of the invention is with the formula $Na_xK_yNbO_3$, $0 \leq x \leq 0.8$, $0.2 \leq y \leq 1$, $x+y=1$. In a preferred embodiment, the material is of the formula $Na_{0.5}K_{0.5}NbO_3$.

In a second aspect, the invention refers to a method for producing a film comprising a biocompatible material of the formula $Na_xK_yNbO_3$, $0 \leq x \leq 0.8$, $0.2 \leq y \leq 1$, $x+y=1$, comprising the steps of:
(a) providing a Na-precursor and a K-precursor for $Na_xK_yNbO_3$;
(b) mixing the precursors in solution, whereby they first react to form a sol and thereafter a gel;
(c) depositing the gel to a substrate in order to obtain a film;
(d) heat treating the gel to obtain an oxide of the material $Na_xK_yNbO_3$, $0 \leq x \leq 0.8$, $0.2 \leq y \leq 1$, $x+y=1$;
(e) if necessary, repeating steps (c) and (d).

The production of a thin film with the $Na_xK_yNbO_3$ material is performed by the use of a sol-gel method, where the substrate is covered by the gel, e.g. by dipping (or spraying, or spinning). The material on the substrate is heat-treated at an elevated temperature (300-900° C.) to form the right composition and crystallinity after the coating procedure. The procedure of dipping, drying and firing can be repeated a number of times until an even film with the desired thickness is produced without cracks or holes.

The morphology is also controlled by using adequate heat treatment conditions, while the composition in the deposited material is controlled by manipulating the molar amount of the starting material. Also, by using sol-gel a substrate having basically any geometry can be deposited, which is not possible with other techniques. Moreover, by using sol-gel the composition of matter can be controlled to a higher degree than with other techniques.

The selection of precursor materials is very important in sol-gel synthesis and there are many possibilities. The group of alkoxides is based on many considerations the best precursors. These consist of metal ions bound to alkoxide groups (OR, deprotonated alcohols). A series of hydrolysis and condensation reactions is started by adding water. During hydrolysis alkoxide groups (OR) are changed to hydroxyl groups, which then react with other alkoxide molecules in condensation reactions and form M-O-M bonds (reaction scheme 1; simplified illustration of hydrolysis (a) and condensation (b-e): M=metal, O=oxygen, H=hydrogen, R=alkyl, ROH=alcohol. Only the groups taking part in the reactions are shown).

(a) M-OR+$H_2$O→M-OH+ROH
(b) M-OH+M-OR→M-0-M+ROH
(c) M-OH+M-OH→M-O-M+$H_2$O
(d) M-OH+M-O(H)R→M-0-M+ROH
(e) M-OH+M-0$H_2$→M-0-M+$H_2$O

Alkoxides are very reactive and forms therefore very pure gels where the organic groups are almost entirely removed by hydrolysis and evaporated. The high reactivity of metal alkoxides often makes the moisture in the air sufficient to obtain fast hydrolysis and condensation. This has been utilized in this invention. Another benefit from using alkoxides is the possibility to prepare heterometallic-alkoxide molecules that comprise two or more different metal ions in the same molecule, which allows a simultaneous hydrolysis of the different alkoxides and thereby is the atomic composition from the solution preserved in the gel.

Hydrolysis and condensation reactions thus form M-O-M bonds and larger units are successively created. Long polymers or large clusters are formed (i.e. a sol) through further condensation in the solution and a network, i.e. a gel, is formed. The gel normally contains hydroxo and some alkoxo groups besides the M-0-M network and the encapsulated solvent. During drying of the gel (solvents and water are evaporated), it often cracks and collapses to a fine powder and this xerogel powder (xero=dry) is thereafter annealed to form an oxide.

Possible precursor compounds for sol-gel preparation of NKN include alkoxides, alcohols, carboxylates, nitrates and citrates. Citrates and nitrates have the advantage that they are water-soluble. The R-group in alkoxides, alcohols and carboxylates can be any alkyl group. Examples of alkoxides include ethoxides, metoxides, isopropoxide isobutoxide and metoxyetoxides. Examples of carboxylates include acetate (ethanoate), propionate and oxalates. It should be bared in mind that the carboxylate, nitrate. and citrate salts will react in a different way compared to alkoxides. Other salts can also be used e.g. acetylacetonate. Mixtures of different type of precursors can also be used; two examples are Nb-alkoxide+ acetate and Nb-alcohols+acetate. It should be noted that (i) nitrates and citrates have to be used in water or water mixtures with polar solvents and (ii) oxalates may be difficult to dissolve. Furthermore, chlorides are commonly used for sol-gel synthesis but are not good precursor candidates for NKN since NaCl will most likely form, which will be difficult to remove.

In a preferred embodiment according to the first and second aspect, the precursors are NaNb(OEt)$_6$ and KNb(OEt)$_6$.

All dry organic solvents are possible as candidates in a sol-gel synthesis of NKN. Examples are alcohols, toluene, hexane, pure ethanol, isopropanol, metoxyetanol, etoxymetanol and ethers. A mixture between a polar and a non-polar solvent are commonly used. The solvents used are to a large extent determined by the precursors used. Certain precursors rewire water based solutions. Halogenated solvents are not suitable, since these will react with the ethoxides.

Maximum temperature is determined by the choice of substrate and evaporation of Na- and K-oxides. Thermogravimetry shows that temperatures up to 1200° C. can be used. Heating rates from 1-100° C. min$^{-1}$ can be used and rates of 10 or 20° C. min$^{-1}$ are preferred. However, even higher heating rates up to 2000° C. min$^{-1}$ may be used should it for instance be desired to shorten the process time. The heating program used can have one or several annealing steps at temperatures up to 1200° C. for any amount of time.

In a preferred embodiment, the heat treatment includes an annealing step or constant temperature plateau in the interval 200-400° C. for 30-120 minutes, most preferably at 300° C.

In another preferred embodiment, the heat treatment includes a temperature gradient from about 300 to about 700° C. at 10-30° C./min.

In yet another preferred embodiment, the heat treatment includes a constant temperature plateau in the interval from 700° C. to 1200° C. for 30-90 minutes, most preferably at 700° C.

In yet another aspect, the invention refers to a biocompatible material comprising Na$_x$K$_y$NbO$_3$, $0 \leq x \leq 0.8$, $0.2 \leq y \leq 1$, $x+y=1$, characterized by that it is obtained by a method according to the invention.

In preferred embodiments, the biocompatible material has a piezoelectric constant $d_{33}$ of at least 20 pC/N, preferably of at least 50 pC/N, more preferably of at least 100 pC/N, even more preferably of at least 150 pC/N, and most preferably of at least 160 pC/N. Further, the material has preferably a relative density that exceeds 97% and a pore size that is less than 4 μm.

In still another aspect, the invention refers to a biocompatible film essentially composed of the biocompatible material of the invention.

In still another aspect, the invention refers to an implant that may come into contact with body tissue and/or body fluids, comprising the biocompatible material of the invention or the biocompatible film of the invention.

In a preferred embodiment, said implant is in the form of a piezoelectric electrode and/or sensor for implantation in the body of a patient for sensing physiological variables. For instance, the material may be used as a layer covering the conducting tip on an electrode for sensing/stimulating cardiac tissue, this layer being in direct contact with conducting liquid in blood/tissue. The conducting tip then will function as one plate of a capacitor and the liquid as the other plate, the piezo material being the dielectric. The layer thus will react to a charge applied onto the plates by generating a mechanical force. The layer will also generate a charge if a mechanical force is applied. By these means the cardiac tissue may be stimulated mechanically as well as electrically when a stimulating pulse is applied to the electrode. Conversely a pressure variation in the blood or a myocardial contraction will generate a charge that can be utilized for sensing purposes. Also, said implant may be used for monitoring motion exerted by the patient.

As used herein, "substrate" means any solid surface on which the material or film of the invention is deposited. This material can be made of any electronically conducting material. Examples of material types include metals, alloys, ceramics, composites and conducting polymers.

Preferably, the substrate material is chosen from Pt or Pt/TiO$_2$/SiO$_2$/Si.

For further substrate variants, see W099/53972 and W099/54266, which hereby is incorporated as a reference.

Air, moisturized air, oxygen gas, moisturized oxygen gas, moisturized nitrogen gas and vacuum up to ultra high vacuum are alternative atmospheres that can be used in the sol-gel method of the invention.

Any method of deposition of NKN precursors on the substrate can be used in the process. For example, dip, spin and spray coating. Dip or spin coatings are preferred.

Spin coating, for example, can be used to prepare films with sol-gel technique. The alkoxide solution is then deposited on a substrate that rotates with high velocity. A gel is formed as a consequence of fast solvent evaporation and rapid reactions with water from the surrounding air as a drop of alkoxide solution hits the rotating substrate and the excess of alkoxide solution is removed simultaneously. It is important to control the structure and composition of the gel to prevent formation of cracks in the film during drying and heat treatment. This is controlled by precursor selection, solution concentration, rotation speed, air moisture, solvent selection and thermal treatment and atmosphere.

For a specific application, the preferred film thickness may e.g. be 0.1-10 μm. Single or multilayer deposition can be used. Multilayer deposition can give 20-300 nm NKN per deposited layer. The number of layers will determine the total film thickness.

The material of the invention can be used in several ways in the medical field. Due to its strength and durability the material can be used as a rigid implant material in either bulk form or in the form of films or layers covering other materials.

The material according to the invention is easily polarized as is well known in the art in order to make it piezoelectric and thus can be used for several different implant applications, such as pressure sensors, accelerometers measuring patient motion or motion of a cardiac wall (force measurement of heart strokes)

The invention will now be further illustrated by way of examples. These examples are only intended to exemplify the invention, and should therefore not be regarded as limitations of the scope of the invention.

EXAMPLE

Sol-Gel Preparation of Na$_{0.5}$K$_{0.5}$NbO$_3$ Films

Example 1

Sol-Gel-Synthesis of Na$_{0.5}$K$_{0.5}$NbO$_3$

Two synthesis paths have been used: preparation of the binary alkoxides separately and then mixing them or preparation of one solution with the precursors mixed directly. The later way was used for film preparation, while the first way was used for the temperature study of the phase transitions as described below). The phase evolution from gel to oxide has been studied on air hydrolyzed powders and the films have been manufactured using spin-coating.
(A) Preparation of Precursors Alkoxides like NaNb(OEt)$_6$ and KNb(OEt)$_6$ are very sensitive to moisture and also to some extent to oxygen. Precautions must therefore be taken during handling and preparation of these compounds. The preparation must be done in inert atmosphere and all glassware, solvents and starting materials were dried prior to usage. The synthesizes were done in an Ar(g) glove-box. The solvents ethanol and toluene were distillated over CaH$_2$ in nitrogen atmosphere to remove water. It can be noted, that simpler equipment and drying processes were used during process development. The binary alkoxides were prepared from Na-metal, K-metal and Nb(OEt)$_5$. The weighing of blank Na and K were also made in the glove-box. Furthermore, the concentration of Nb(OEt)$_5$ was determined before usage. This was done by gravimetric analysis of Nb$_2$O$_5$ after hydrolysis and heating to 1000° C. for 1 h of an exact volume of the Nb(OEt)$_5$ solution.

Synthesis of NaNb(OEt)$_6$ and KNb(OEt)$_6$ were made as described below:

NaNb(OEt)$_6$: 0.500 g (0.0218 mol) Na was dissolved in 20 ml toluene:ethanol 1:1 during hydrogen gas evolution according to:

Na+EtOH→Na(OEt)+0.5H 6.915 g (0.0218 mol) Nb(OEt)$_5$ was then added to the solution and it was stirred over night. The solvents were evaporated under reduced pressure after that and white crystals of NaNb(OEt)$_6$ were obtained.

KNb(OEt)$_6$: 1.000 g K (0.02558 mol) was dissolved in 20 ml toluene:ethanol 1:1 during hydrogen gas evolution according to:

K+EtOH→K(OEt)+0.5H$_2$ 8.132 g (0.02558 mol) Nb(OEt)$_5$ was then added and the solution was stirred over night. The solvents were evaporated under reduced pressure after that and white crystals of KNb(OEt)$_6$ were obtained.

For the preparation of Na$_{0.5}$K$_{0.5}$NbO$_3$ a solution of (Na$_{0.5}$K$_{0.5}$)Nb(OEt)$_6$ in toluene:ethanol 1:1 has been used. This is easily prepared by dissolving NaNb(OEt)6 and KNb(OEt)$_6$ crystals, or directly, without preceding crystallization, by dissolving equal moles of Na and K together with toluene:ethanol and then adding Nb(OEt)$_5$.

(B) From Gel to Oxide—Phase Development Studies of Powder.
(i) Gel

Figure 2:
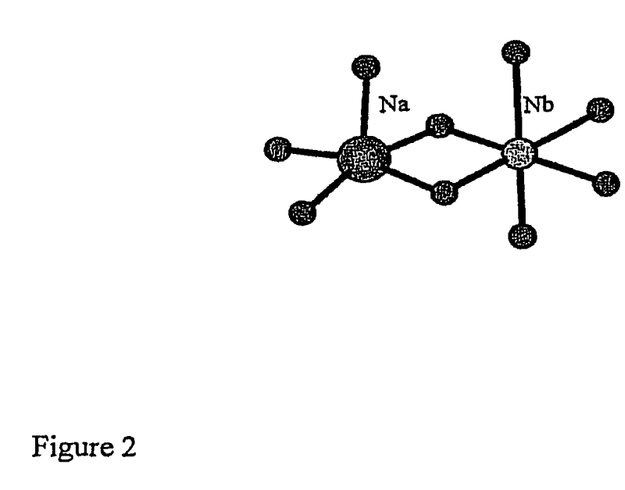
FIG. 2 shows the probable structure of $NaNb(OEt)_6$ and $KNb(OEt)_6$ in solution.

The gels are light yellow and amorphous according to X-ray diffraction (XRD). IR spectroscopy studies show that the gels do not contain any organic groups, i.e. all alkoxide groups have reacted during the hydrolysis reactions and the solvents have evaporated. IR spectroscopy (4000-450 cm$^{-1}$) shows that the gels contain water and carbonate groups (FIG. 2). The later originates from CO$_2$ adsorption from air. There are absorption bands from M-O stretching modes, mainly from Nb—O, in the range around 1000 cm$^{-1}$.
(ii) Heat Treatment To study the phase transitions during heat treatment it is more effective to study powder than thin films, since TGA can be used to determine at which temperatures reactions take place and also indicate at what temperature pure oxide is formed. XRD of powder can also more easily be done at high resolution compared to thin films and IR studies can also be used to describe the chemical content.

Heat treatment to transform gel powder to oxide has been studied with thermogravimetry (TG) to 1000° C. in air and oxygen, using different heating rates. Both new and aged gels were studied. The gels were prepared using hydrolysis in air: the alkoxide solution was deposited in a thin layer on a glass substrate and allowed to react with moisture in the air. Some gels were also treated with water vapor. TG studies of air hydrolyzed binary K—Nb and Na—Nb gels are compared in FIG. 3.

Figure 3:
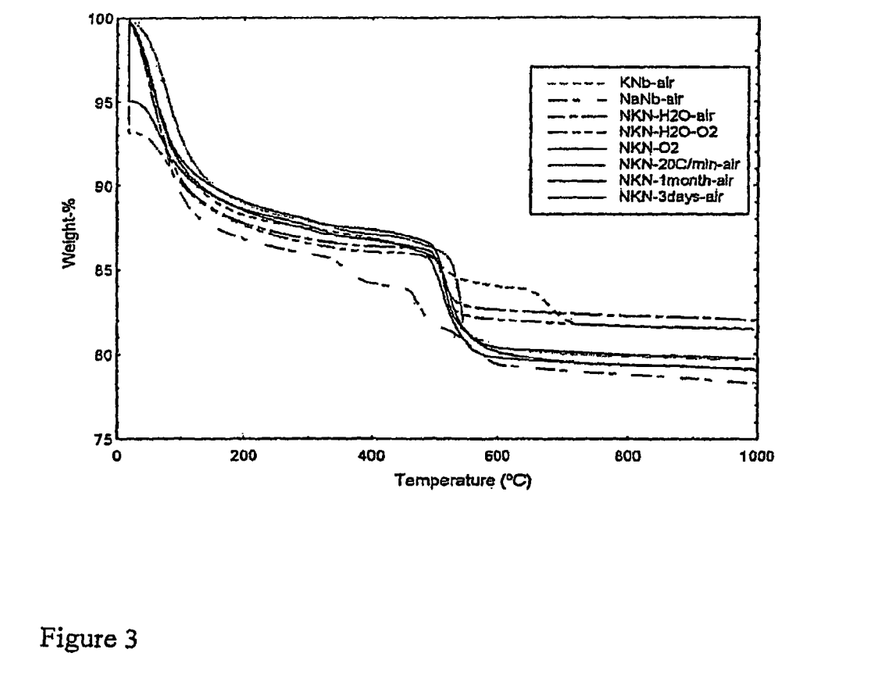
FIG. 3 shows thermogravimetric studies of gels wherein the heating rate is 5° C.-min$^{-1}$ unless otherwise stated.

The TG investigations show that the weight loss for Na—K—Nb gels occur in three steps: (i) the gel loses 10-12% of it weight in the first step from room temperature to ca. 170° C., (ii) a smaller weight loss, approximately 2-4% takes place from ca. 170° C. to ca. 500° C., and (iii) the last steep slope occurs between 500 and 550 or 580° C., and the sample loses <0.5% of its initial weight from 600 to 1000° C. This pattern is the same regardless of hydrolysis path, heating rate and atmosphere used. On the contrary, water vapor treatment of the gel affects the size of the weight loss in the last step: air hydrolyzed gels then lose ca. 7% between 500 and 550° C., while gels treated with water vapor lose only ca 4% from 500 to 580° C.

The air hydrolyzed K—Nb gel shows the same behavior as Na—K—Nb gels up to 400° C., followed by a weight loss of ca. 4% in two steps (2% in each step) taking place from 400 to 550° C. and from 620 to 700° C., respectively, and thereafter the curve flattens out. The Na—Nb gel shows the same behavior as the Na—K—Nb gels up to ca 320° C., and then losses ca 7% in three steps from 320 to 600° C., followed by a further weight loss of 1% between 600 and 1000° C.

This shows that the K—Nb gels decomposition occurs faster together with the Na—Nb gel, indicating good homogeneity, since a bad mixing of the two gels would give raise to the step at 700° C. that only occurs in K—Nb gel.

The air hydrolyzed Na—K—Nb gels have been heated to 170, 300, 500, 550, 600, 700 and 1000° C., respectively, to study the phase evolution during heating. These samples were then analyzed by IR spectroscopy and XRD.

Figure 4:
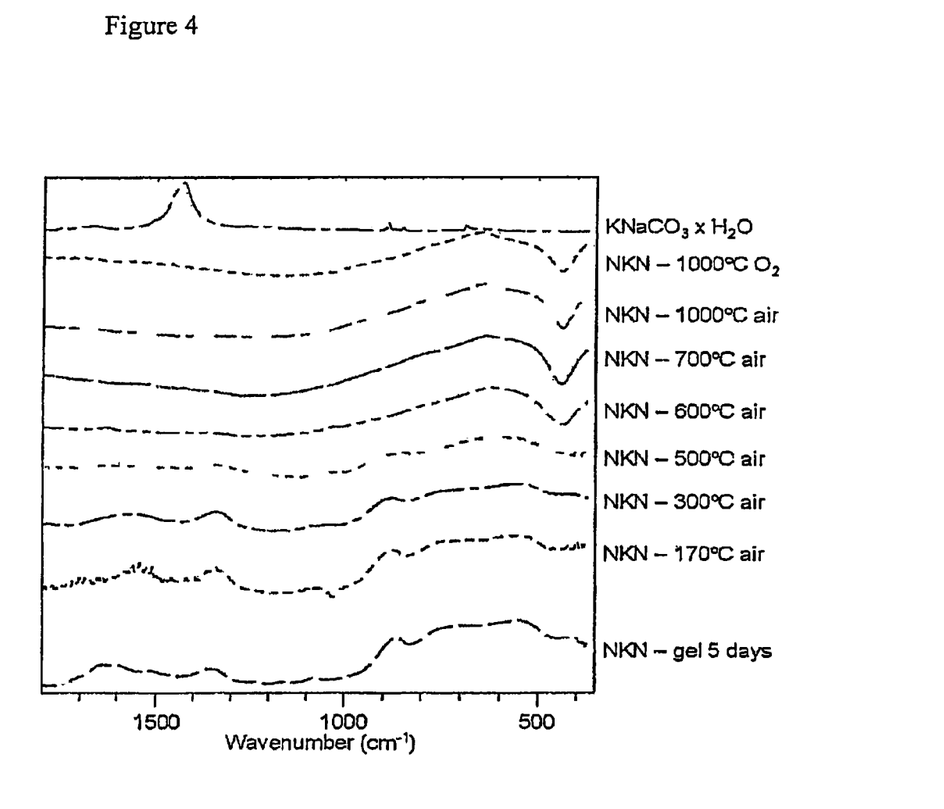
FIG. 4 shows IR spectra of gels and samples heated to different temperatures.

The IR studies (FIG. 4) together with the TG results show that the two first steps up to 500° C. originate from water disappearance (by a combination of evaporation and condensation reactions) and that the third step derives from decomposition of carbonates to oxide and carbon dioxide. In some samples small amounts of carbonates were still detected at 600° C., however, these were completely removed at 700° C.

Figure 5:
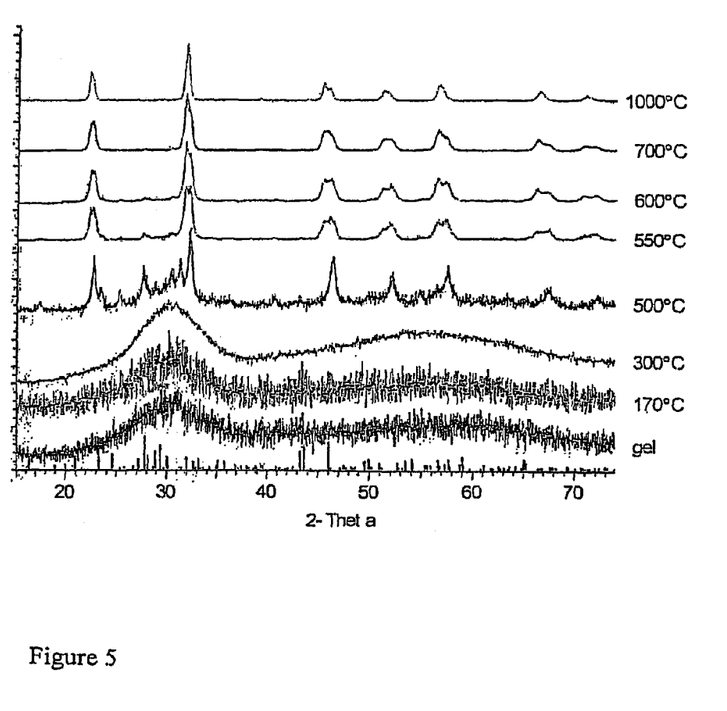
FIG. 5 shows powder XRD diffractograms of gels and samples heated to different temperatures.

The XRD results showed that the samples were amorphous up to 300° C., and that crystallization had started at 500° C.; the diffractogram shows peaks from perovskite (similar to the preferred NKN phase), however, unidentified peaks from one or more other phases were also detected. The peaks from these additional phase/s decrease and the peaks from perovskite increase with temperature. Small peaks that do not correspond to perovskite are discernible in the diffraction pattern from the samples heat treated at 550 and 600° C. These peaks are not detected and pure perovskite is obtained at 700° C. The perovskite peaks are better defined after heating to 1000° C., most likely due to improved crystallization. No trace of additional phase/s was observed for the sample treated at 1000° C. (FIG. 5).

(C) Production of Films

Design of the temperature programs for film preparation was based on the results from the powder studies. The films on flat Pt—Pt/TiO2/SiO2/Si-substrate have been prepared by spin coating in air (spin rate 3200-3300 rpm, time 40 s). Toluene:ethanol 1:1 solutions of $(Na_{0.5}K_{0.5})Nb(OEt)_6$ with the concentrations 0.3 and 0.6 mol·dm$^{-3}$ were used.

A gel film is formed as a result of solvent evaporation and reactions with water in the air during spin coating. From the phase development studies using powders, it can be concluded that the gel needs to be heated to at least 700° C. to form pure perovskite. The gel was therefore transformed to oxide by heating in air to 700° C. Several different heating rates and programs were tested.

Figure 6:
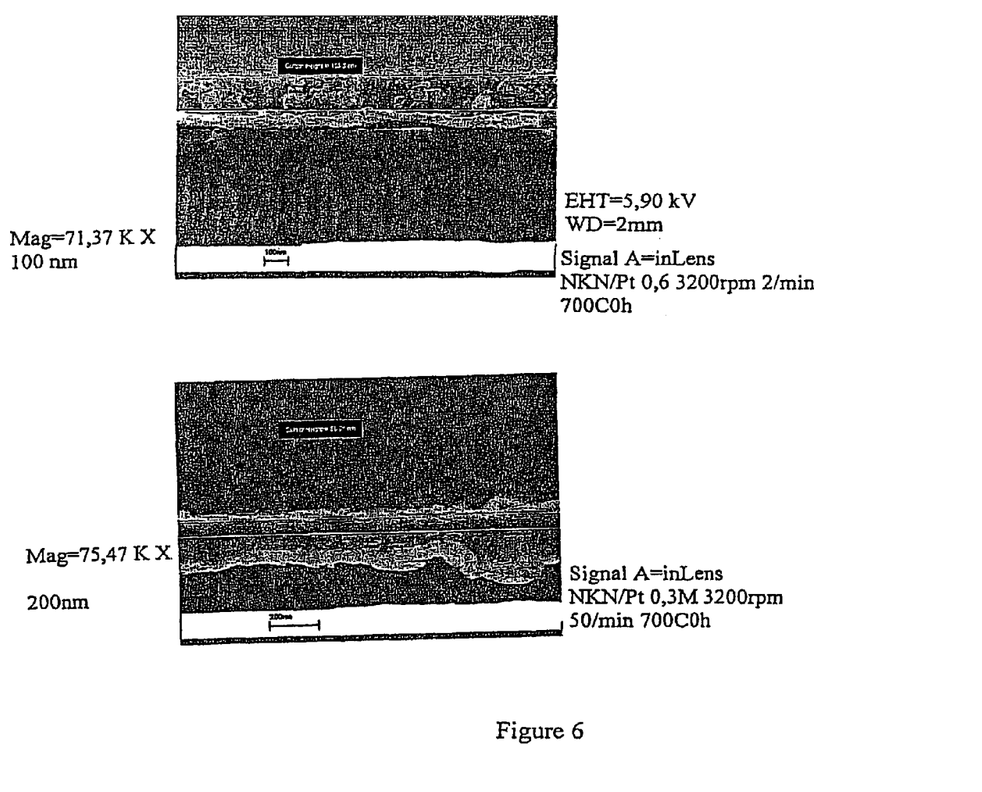
FIG. 6 shows SEM micrographs showing the cross section of the NKN-films on $Pt/TiO_2/SiO_2$ substrate prepared using solutions with the concentrations 0.6 mol-dm$^{-3}$ (a) and 0.3 mol-dm$^{-3}$ (b).
Figure 7:
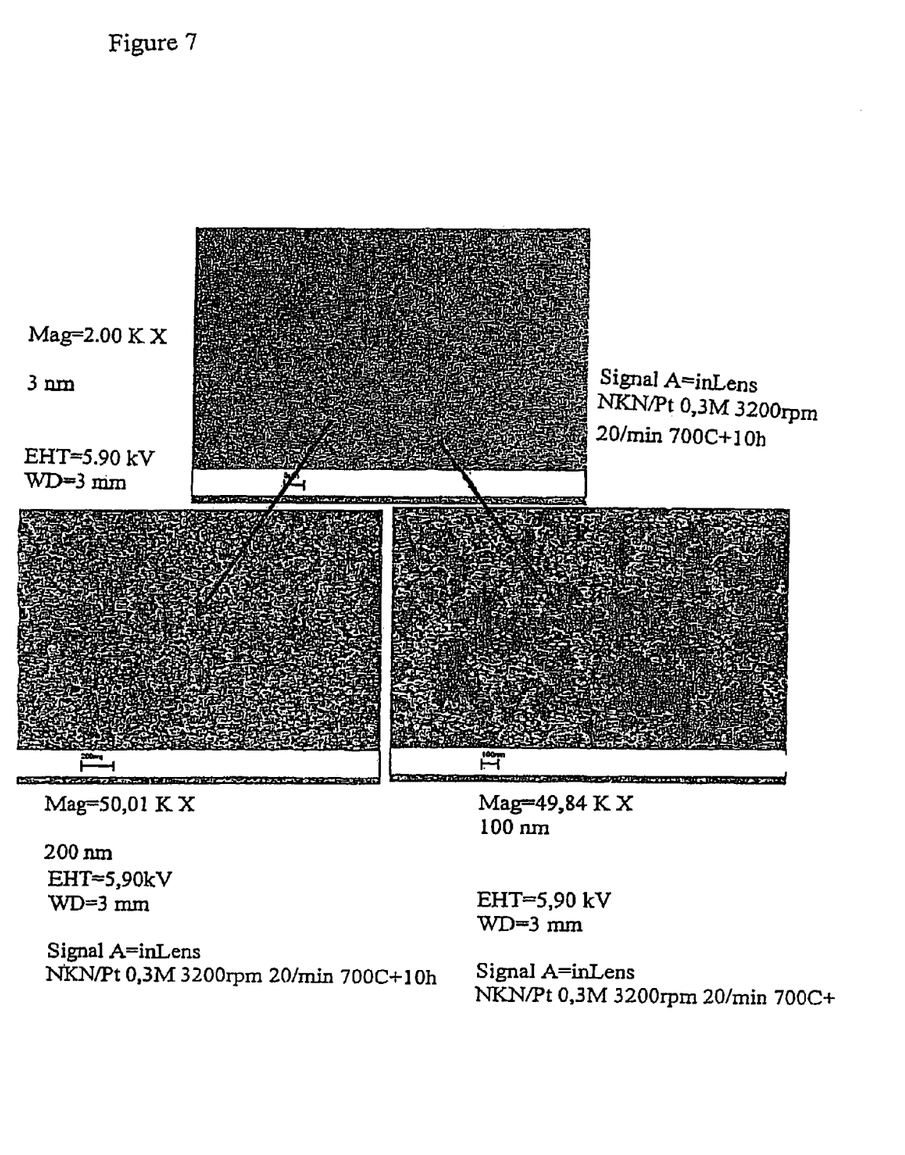
FIG. 7 shows an SEM micrograph showing a typical NKN-film prepared on $Pt/TiO_2/SiO_2$ substrate, wherein types of crystals can be seen.
Figure 8:
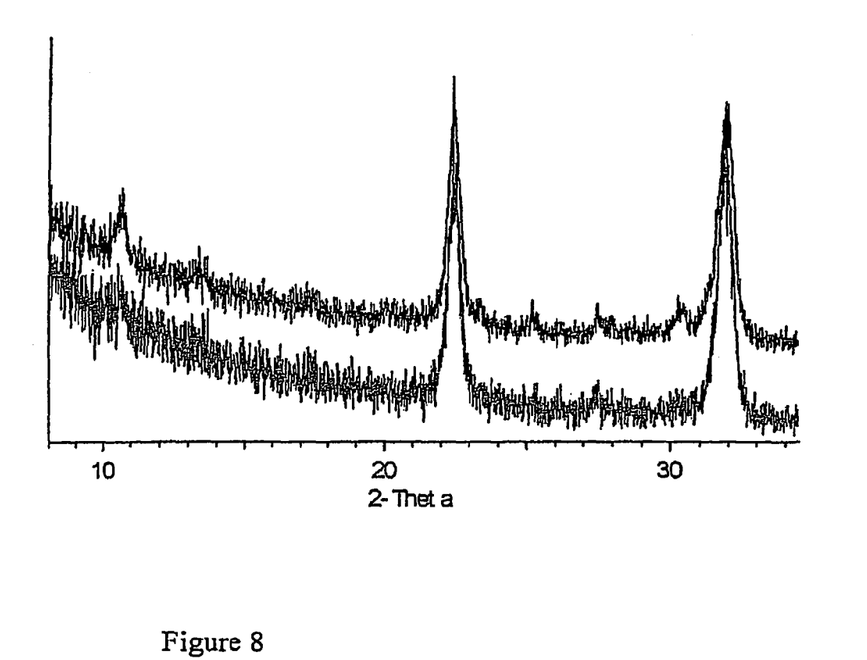
FIG. 8 shows Gracing Incidence (GI) XRD diffractograms of films prepared using heating program A and a constant heating rate 20° C.-min$^{-1}$ to 700° C.

The oxide films were investigated using Scanning Electron Microscopy (SEM) and X-ray Diffraction (XRD). SEM shows that the film thicknesses were 150-160 nm and 60-70 nm, respectively for the films prepared from a solution with the concentration 0.6 mol·dm$^{-3}$ and 0.3 mol·dm$^{-3}$, respectively (FIG. 6). SEM also shows that the films consist of two types of crystals (FIG. 7), indicating that two different phases have been formed. The formation of two different phases in the films is confirmed by XRD (FIG. 8). The perovskite phase was identified together with a varying amount of $(Na,K)_4Nb_6O_{17}$ in all films.

Figure 9:
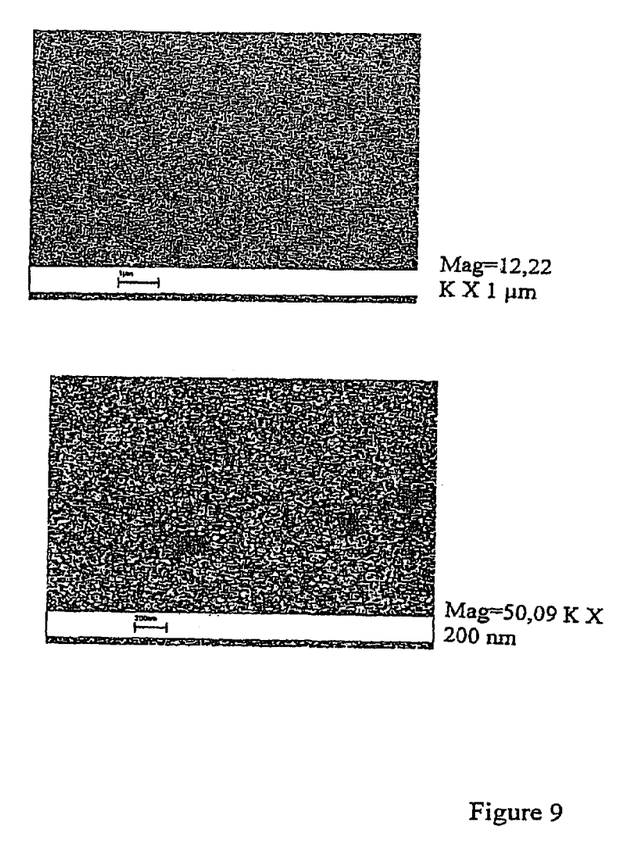
FIG. 9 shows SEM micrographs of films prepared using heating program A.

The heating program (A) that gave a high phase purity was used to prepared thick films by multi layer deposition of 0.5 mol-dm-3 on thin Pt substrates. Heating program A consists of the following steps: heating from room temperature to 300° C. at 10° C.·min$^{-1}$, annealing at 300° C. for 50 min, heating from 300° C. to 700° C. at 20° C.·min$^{-1}$, annealing at 700° C. for 60 min and free cooling to room temperature. The program has a plateau at 300° C. to improve the condensation reactions without crystallization of the gel. This was followed by fast heating to 700° C., passing the critical 500° C. range rapidly. The phase evolution studies showed that the $(Na,K)_4Nb_6O_{17}$ phase was found to be formed in the 500° C. range and that a pure and carbonate free oxide was formed at 700° C. To achieve a complete decomposition of all carbonates and a higher density the films were sintered at 700° C. for 60 min. The heating program A gave significantly smaller amounts of the $(Na,K)_4Nb_6O_{17}$ phase, see FIGS. 8 and 9.

It can be noted, that tests using 90 or 30 min annealing at 300° C. gave inferior result compared to program A. Furthermore, results indicate that a longer annealing time (2-10 h) at 700° C. improves the phase purity further.

Although modifications and changes may be suggested by those skilled in the art, it is the intention of the inventors to embody within the patent warranted hereon all changes and modifications as reasonably and properly come within the scope of their contribution to the art.

What is claimed is:

1. Method for producing a film comprising a biocompatible material of the formula $Na_xK_yNbO_3$, $0 \leq x \leq 0.8$, $0.2 \leq y \leq 1$, $x+y=1$, comprising:
    a) providing a Na-precursor and a K-precursor for $Na_xK_yNbO_3$ wherein the precursors are $NaNb(OEt)_6$ and $KNb(OEt)_6$;
    b) mixing the precursors in solution, wherein said precursors first react to form a sol and thereafter a gel;
    c) depositing the gel to a substrate to produce a film;
    d) heat treating the gel in the film at a temperature increasing from 200 to 1200° C. to obtain an oxide of the material $Na_xK_yNbO_3$, $0 \leq x \leq 0.8$, $0.2 \leq y \leq 1$, $x+y=1$; and
    e) if necessary, repeating steps (c) and (d).

2. Method according to claim 1, comprising heat treating the gel at a heating rate of 1-2000° C. min$^{-1}$.

3. Method according to claim 1, comprising heat treating the gel at a heating rate of 1-100° C. min$^{-1}$.

4. Method according to claim 1, comprising heat treating the gel at a heating rate of 10-20° C. min$^{-1}$.

5. Method according to claim 1, comprising heat treating the gel at a temperature gradient from about 300 to about 700° C. at 10-30° C. min$^{-1}$.

6. Method according to claim 1, comprising heat treating the gel with a heating profile comprising at least one constant temperature plateau.

7. Method according to claim 1, comprising heat treating the gel with a heating profile comprising at least a constant temperature plateau in a range of 200-400° C. for 30-120 minutes.

8. Method according to claim 1, comprising heat treating the gel with a heating profile comprising at least a constant temperature plateau in a range of 700-1200° C. for 30-120 minutes.

9. Method according to claim 1, wherein the precursors are prepared in an inert atmosphere.

10. Method for producing a film comprising a biocompatible material of the formula $Na_xK_yNbO_3$, $0 \leq x \leq 0.8$, $0.2 \leq y \leq 1$, $x+y=1$, comprising:
   a) providing a Na-precursor and a K-precursor for $Na_xK_yNbO_3$;
   b) mixing the precursors in solution, wherein said precursors first react to form a sol and thereafter a gel, wherein mixing the precursors in solution comprises a solution of $(Na_{0.5}K_{0.5})Nb(OEt)_6$ in toluene:ethanol 1:1, and wherein $NaNb(OEt)_6$ and $KNb(OEt)_6$ crystals are dissolved;
   c) depositing the gel to a substrate to produce a film;
   d) heat treating the gel in the film at a temperature increasing from 200 to 1200° C. to obtain an oxide of the material $Na_xK_yNbO_3$, $0 \leq x \leq 0.8$, $0.2 \leq y \leq 1$, $x+y=1$; and
   e) if necessary, repeating steps (c) and (d).

11. Method according to claim 10, comprising heat treating the gel at a heating rate of 1-2000° C. $min^{-1}$.

12. Method according to claim 10, comprising heat treating the gel at a heating rate of 1-100° C. $min^{-1}$.

13. Method according to claim 10, comprising heat treating the gel at a heating rate of 10-20° C. $min^{-1}$.

14. Method according to claim 10, comprising heat treating the gel at a temperature gradient from about 300 to about 700° C. at 10-30° C. $min^{-1}$.

15. Method for producing a film comprising a biocompatible material of the formula $Na_xK_yNbO_3$, $0 \leq x \leq 0.8$, $0.2 \leq y \leq 1$, $x+y=1$, comprising:
   a) providing a Na-precursor and a K-precursor for $Na_xK_yNbO_3$;
   b) mixing the precursors in solution, wherein said precursors first react to form a sol and thereafter a gel, wherein mixing the precursors in solution comprises a solution of $(Na_{0.5}K_{0.5})Nb(OEt)_6$ in toluene:ethanol 1:1, and wherein equal moles of Na and K are dissolved together with toluene:ethanol and then adding $NaNb(OEt)_5$;
   c) depositing the gel to a substrate to produce a film;
   d) heat treating the gel in the film at a temperature increasing from 200 to 1200° C. to obtain an oxide of the material $Na_xK_yNbO_3$, $0 \leq x \leq 0.8$, $0.2 \leq y \leq 1$, $x+y=1$; and
   e) if necessary, repeating steps (c) and (d).

16. Method according to claim 15, comprising heat treating the gel at a heating rate of 1-2000° C. $min^{-1}$.

17. Method according to claim 15, comprising heat treating the gel at a heating rate of 1-100° C. $min^{-1}$.

18. Method according to claim 15, comprising heat treating the gel at a heating rate of 10-20° C. $min^{-1}$.

19. Method according to claim 15, comprising heat treating the gel at a temperature gradient from about 300 to about 700° C. at 10-30° C. $min^{-1}$.

* * * * *